United States Patent [19]

Iqbal

[11] 3,944,615

[45] Mar. 16, 1976

[54] PROCESS FOR THE PRODUCTION OF AROMATIC PRIMARY AMINES

[75] Inventor: Abul F. M. Iqbal, Glattbrugg, Switzerland

[73] Assignee: Monsanto Company, St. Louis, Mo.

[22] Filed: May 23, 1974

[21] Appl. No.: 472,762

Related U.S. Application Data

[63] Continuation-in-part of Ser. No. 246,216, April 21, 1972, abandoned.

[30] Foreign Application Priority Data

Apr. 30, 1971  Switzerland.......................... 6379/71

[52] U.S. Cl. ............................................. 260/580
[51] Int. Cl.² ....................................... C07C 85/11
[58] Field of Search ..................................... 260/580

[56] References Cited
UNITED STATES PATENTS

| | | | |
|---|---|---|---|
| 2,772,313 | 11/1956 | Trager | 260/580 |
| 2,867,628 | 1/1959 | Cass | 260/580 X |
| 3,051,753 | 8/1962 | Dietzler et al. | 260/580 |
| 3,194,839 | 7/1965 | Robinson et al. | 260/580 X |
| 3,678,108 | 7/1972 | Arrigo et al. | 260/580 X |

*Primary Examiner*—Paul F. Shaver

[57] ABSTRACT

Aromatic primary amines, e.g., aniline, are prepared by reduction of an aromatic nitro compound, e.g., nitrobenzene with carbon monoxide and water in the presence of a basic nitrogen containing compound selected from the group consisting of tertiary amine and amide and a rhodium catalyst selected from the group consisting of rhodium oxide, rhodium hydroxide, rhodium carbonyl compound and rhodium salt which forms a rhodium carbonyl compound under reduction conditions.

12 Claims, No Drawings

PROCESS FOR THE PRODUCTION OF AROMATIC PRIMARY AMINES

The present patent application is a continuation-in-part of Serial No. 246,216, filed April 21, 1972, now abandoned.

BACKGROUND OF THE INVENTION

1. Field of the Invention

This invention relates to a process for the production of aromatic primary amines from aromatic nitro compounds. In a particular aspect this invention relates to the preparation of an aromatic primary amine by reduction of the corresponding aromatic nitro compound with carbon monoxide and water in the presence of a basic nitrogen-containing compound which is a tertiary amine or an amide and a rhodium catalyst which is rhodium oxide, rhodium hydroxide, rhodium carbonyl including derivatives thereof or rhodium salt which forms a rhodium carbonyl under reduction reaction conditions.

2. Description of the Prior Art

The reduction of aromatic nitro compounds to primary amines with carbon monoxide and water as reducing agent in the presence of a catalytic composition comprising oxygenated compounds of at least two metals, selected from the group consisting of titanium, vanadium, manganese, iron, cobalt, nickel, copper, germanium, zirconium, molybdenum, silver, tin, antimony, lanthanum, cerum, neodymium, tungsten, gold, mercury, thallium, lead, bismuth and thorium is known from British Pat. No. 1,201,050 (Aug. 5, 1970). In this process in the reduction of nitrobenzene hydrogen and carbon monoxide are employed as the reducing agent with yields of aniline in the range of from 5 to 41% being obtained. An additional disadvantage of the process using hydrogen and carbon monoxide is that the catalytic composition is difficult and laborious to prepare.

From U.S. Pat. No. 2,671,807 (issued Mar. 9, 1954) it is known that undefined mixtures of amines are obtained by high (>500 atm.) pressure reduction of aromatic nitro compounds with carbon monoxide and hydrogen in the presence of certain nickel, cobalt and ruthenium carbonyl catalysts. German Pat. No. 441,179 (Feb. 26, 1927) shows that aniline resulted from reduction of nitrobenzene in the presence of alkaline iron carbonyl solutions with the system being essentially stoichiometric.

The use of rhodium metal or certain rhodium compounds as catalysts in the reduction of aromatic nitro compounds is also known. For example the synthesis of urethanes by reaction of nitrobenzene and carbon monoxide in alcohols or phenols in the presence of $[Rh(CO)_2Cl]_2$ and a Lewis acid as co-catalyst is described in British Patent 993,704 (June 2, 1965). Also the reduction of nitrobenzene with carbon monoxide in the presence of a catalyst consisting of rhodium, charcoal and $FeCl_3$ has been reported by W. P. Hardy et. al. to yield phenylisocyanate. [See Tetrahedron Letters p. 961 (1967).]

SUMMARY OF THE INVENTION

It has now been discovered in accordance with the process of the present invention that aromatic primary amines are obtained by reduction of aromatic nitro compounds using as reducing agent carbon monoxide and water in the presence of a basic nitrogen containing compound which is a tertiary amine or an amide and a rhodium catalyst which is rhodium oxide, rhodium hydroxide, rhodium carbonyl and rhodium salt which forms a rhodium carbonyl compound under reduction reaction conditions.

The process of the present invention permits the production of aromatic primary amines from aromatic nitro compounds in improved yields and at temperatures and pressures lower than those employed in prior art reduction procedures. The process of the present invention does not require the employment of hydrogen since the reducing agent is carbon monoxide and water.

DETAILED DESCRIPTION OF THE INVENTION

Any suitable aromatic nitro compound can be employed in the process of the present invention. Suitable compounds include water insoluble nitro compounds for example p-nitrobenzene, 3,4-dichloro-nitrobenzene, p-nitrobenzoic acid ethylester, m-nitrobenzene and -nitroanisole, as well as water-soluble nitro compounds, for example m-nitrobenzene sulfonic acid, 1-nitronaphthalene -6-, -7- and -8- sulfonic acid, and 1-nitronaphthalene-3,6,8-trisulfonic acid.

The rhodium catalyst employed in the process of the present invention is selected from the group consisting of a rhodium oxide, rhodium hydroxide, a rhodium carbonyl compound (including rhodium carbonyl derivatives) and a rhodium salt which forms a rhodium carbonyl compound under reduction reaction conditions. Examples of suitable rhodium catalysts include $RhO_2$ and $Rh_2O_3$ (rhodium oxides); $RhO_2.2H_2O$ and $Rh_2O_3.5H_2O$ (rhodium hydroxides); $[Rh(CO)_2Cl]_2$, $RhCl_2.RhO.3CO$, $Rh_4(CO)_{12}$ and $Rh_6(CO)_{16}$ (rhodium carbonyl compounds); and $RhCl_3$, $RhI$, $RhCl_3.3H_2O$ and $Rh(NO_3)_3$ (rhodium salts). The above-referred to classes of rhodium catalysts and methods for their preparation are well-known to the art.

The amount of suitable rhodium catalyst employed in the process of the present invention can vary over a wide range with the optimum amount depending among other things on the particular catalyst of choice, the particular aromatic nitro compound, and the reduction conditions (temperature and pressure). In all cases a catalytic amount of rhodium catalyst is required. Typically a molar ratio of nitro compound to catalyst is in the range of from about 100:1 to about 10000:1.

The basic nitrogen containing compound employed in the process of the present invention is selected from the group consisting of tertiary amines and amides. Since the nitrogen containing compound additionally serves as a solvent, it should be liquid at the temperature of reaction and preferably should be employed in excess, e.g. 6 or more mols per nitro group. In the case of the tertiary amines useful in the present invention, strong, basic amines having a dissociation constant in aqueous solution of at least $pK_a=10$ are especially preferred. Examples of suitable amines include triethylamine, N,N-dimethylbutylamine, pyridine, N-methylpyrrolidine, n-ethylpiperidine, N,N'dimethylpiperazine, tetramethylurea, pentamethylguanidine, etc. and the like. While not being limited to a particular theory it is believed that the solvent amines enhance the formation and stability of the catalytic species which are believed to be hydrido metal derivatives. In the case of the amides useful in the present invention, weakly basic amides such as dimethylformanide and strongly basic amides such as tetramethylurea more successfully promote the desired reduction than do the simple tertiary amides. Any suitable amide may be employed.

In the process of the present invention, the reducing agent employed in water and carbon monoxide. The amount of reducing agent employed may vary depending principally upon the particular nitro compound to be reduced, with suitable amounts being apparent to the skilled worker in the art. Since water is acting as a hydrogen source, in all cases at least 1 mol of water per nitro group is required with 1 to 3 mols being preferred.

In carrying out the reduction reaction of the present invention a wide range of temperatures and pressures may be employed with the process being conducted under suitable reduction reaction pressure and temperature conditions. A particular advantage of the process of the present invention is that low temperatures in the range of from about 50° to about 150°C and low CO pressures of in the range of from about 50° to about 120 atm. may be employed. If desired, however, lower and higher reduction reaction temperatures and pressures may be employed. When a rhodium oxide is the catalyst of choice and when quantitative yields are desired, temperatures above 150°C and carbon monoxide pressures of 100 atm. and more are preferred. While not being limited to any particular theory, it is believed that such reduction conditions are desired with a rhodium oxide catalyst to promote formation of the desired catalytic rhodium species from the oxide. With rhodium carbonyl compounds, the desired optimum results can be obtained at temperatures as low as 50°–60°C. and at pressures as low as about 50 atm. Under such reduction conditions strongly basic tertiary amines are preferred as the basic nitrogen compound.

The reduction process of the present invention is carried out in the known manner using suitable reduction reaction equipment.

The following examples illustrate specific embodiments of the invention.

EXAMPLE 1

This example shows six runs for the preparation of aniline by reduction of nitrobenzene using $Rh_2O_3$ as the catalyst. Each run was conducted using the following procedure:

Nitrobenzene (12.3 grams - 0.1 mol.), water (5.5 grams-0.3 mole), basic nitrogen containing compound (50–60 ml) carbon monoxide (initial pressure at room temperature) and catalyst (25.4 mg.) were charged to a 0.5 liter stainless steel rocking autoclave. The contents of the autoclave were heated under pressure to the desired temperature and maintained at that temperature during the reaction period. The contents were shaken by rocking of the autoclave during the reaction period. on completion of the reaction period, the contents of the autoclave were cooled, gases were vented and solvent was removed by distillation. The resulting reaction mixture was analyzed for aniline (GLC, IR and NMR spectroscopy analysis). The results are shown in Table 1. These results show the effectiveness of the process of the present invention in the production of aniline at relatively low temperatures and pressures.

TABLE I

| Run No. | Temp. °C. | CO atm | Time (hours) | Conversion % | Aniline yield % | Nitrogen-containing Compound |
|---|---|---|---|---|---|---|
| 1 | 170 | 140 | 3 | 100 | >95 | N-methylpyrrolidine |
| 2 | 150 | 120 | 3 | 85 | ~75 | " |
| 3 | 125 | 100 | 4 | 51 | 42 | " |
| 4 | 100 | 80 | 12 | 17 | 11 | " |
| 5 | 150 | 120 | 3 | 100 | >95 | Pyridine |
| 6 | 125 | 100 | 4 | 48 | 40 | " |

EXAMPLE 2

Ten runs for the preparation of aniline by reduction of nitrobenzene were carried out. In the runs the procedure of Example 1 was followed in all essential detail with the following exceptions: In runs 1, 2, 3, 8 and 9 no basic nitrogen compound was employed. In run 8 water was omitted. In runs 8, 9 and 10 rhodium carbonyl compounds were employed as catalyst. In each run, the CO pressure was 120 atm., the temperature was 150°C and the reaction time was 3 hours. The results are shown in Table 2. From the results it is apparent that the yield of aniline is lower in the absence of basic nitrogen compound and in the absence of water. In run 8 basic nitrogen compound and water were both omitted with a resultant aniline yield of 11%. In run 9 basic nitrogen compound was omitted with a resultant yield of aniline of 34%. In contrast in run 10 both basic nitrogen compound and water were present and the yield of aniline was >90%.

TABLE II

| Run No. | Catalyst | Solvent | Conversion % | Aniline Yield % |
|---|---|---|---|---|
| 1 | $Rh_2O_3$ | Methanol | 6 | 4 |
| 2 | " | " | 26 | 24 |
| 3 | " | Acetone | 31 | 29 |
| 4 | " | THF | 39 | 35 |
| 5 | " | Dimethylformamide | 100 | >95 |
| 6 | " | Pyridine | 100 | >95 |
| 7 | " | N-methylpyrrolidine | ~85 | ~75 |
| 8(b) | $[Rh(CO)_2Cl]_2$ | Methanol | 14 | 11 |
| 9 | " | " | 41 | 34 |
| 10 | " | Pyridine | 100 | 90 |

(b)absence of water

EXAMPLE 3

Seven runs for the preparation of aniline by reduction of nitrobenzene using various rhodium catalysts were carried out following in all essential details the general procedure of Example 1. The results are shown in Table 3.

EXAMPLE 4

3-Nitrotoluene (0.1 mole), hexarhodiumhexadecacarbonyl ($5 \times 10^{-3}$ mole), water (0.3 mole) and N-methylpyrrolidine (50 ml) are charged to an autoclave. The autoclave is sealed and pressurized to 60 atmospheres with carbon monoxide. Agitation is commenced and the autoclave and contents are heated to 50° and kept at this temperature for 10 hours. The autoclave is then cooled and vented and the contents are discharged. Gas-liquid chromatography of the product shows over 95% conversion of the nitro compound to m-toluidine, unequivocally identified by isolation and spectroscopic (ir, nmr) comparison with an authentic sample.

EXAMPLE 5

By a procedure similar to that of Example 4, p-chloronitrobenzene was almost quantitatively converted to p-chloroaniline.

EXAMPLE 6

By a procedure similar to that of Example 4 using tetrarhodiumtetradecacarbonyl in place of hexarhodiumhexadecacarbonyl, p-nitroaniline was reduced to p-phenylenediamine in over 85% yield. When the reaction is carried out in the absence of the basic tertiary amine solvent (N-methylpyrrolidine), only trace amount of p-phenylenediamine was obtained.

EXAMPLE 7

The sodium salt of 1-nitronaphthalene-3,6,8-trisulphonic acid (0.1 mole) and hexarhodiumhexadecacarbonyl ($5 \times 10^{-3}$ mole) in water, 0.8 mole, and N-methylpyrrolidine (50 ml) are charged to an autoclave (0.5 l). The autoclave is sealed and pressurized to 60 atm with carbon monoxide and agitated at 100°C for 8 hours. The autoclave is then cooled and vented and the contents are discharged. Acidification of the product solution subsequent to removal of the tertiary amine solvent gives more than 80% yield of 1-naphthylamine-3,6,8-trisulphonic acid (Koch acid).

EXAMPLE 8

By a procedure identical to that of Example 7, the sodium salt of m-nitrobenzenesulphonic acid was reduced to m-aminobenzenesulphonic acid in 90% yield.

EXAMPLE 9

In place of 3-nitrotoluene of Example 7 there is charged the sodium salt of p-nitrobenzoic acid. A ca. 90% conversion of the nitro compound to p-aminobenzoic acid is obtained.

EXAMPLE 10

By a similar procedure to that of Example 4, 4-nitrodiphenylether is easily reduced to the corresponding aminodiphenylether.

EXAMPLE 11

By following a procedure similar to that of Example 4 using suitable reaction time and temperature, 3-nitrophenol can be reduced to give high yields of 3-aminophenol.

EXAMPLES 12–15

In place of N-methylpyrrolidine of Example 4, there is used triethylamine, 1.2-bis-(dimethylamino)-ethane, trimethylamine, N-methylpiperidine, respectively, as solvent. In all four experiments the yield of m-toluidine exceeded 85–90%.

EXAMPLE 16

Nitrobenzene (0.01 mole), rhodium hydroxide ($5 \times 10^{-3}$ mole), water (0.3 mole) and N-methylpyrrolidine (50 ml) are charged to an 0.5 l autoclave. The autoclave is sealed and pressurized to 100 atmospheres with carbon monoxide. Agitation is commenced and the autoclave and contents are heated to 160°–170° and kept at this temperature for 3 hours. the autoclave is then cooled and vented and the contents are discharged. Gas-liquid chromatography of the product shows over 95% conversion of the nitro compound to aniline.

EXAMPLES 17–19

In place of rhodium hydroxide of Example 16, there is used rhodium acetate, chlorotris (triphenylphosphine)rhodium (I), rhodium trichloride trihydrate, respectively, as catalyst. In all three experiments the yield of aniline exceeded 90%.

EXAMPLE 20

Nitrobenzene (0.1 mole), hexarhodiumhexadecacarbonyl ($5 \times 10^{-3}$ mole), water (0.3 mole) and triethylamine (50 ml) are charged to an autoclave of 0.5 l capacity. The autoclave is sealed and pressurized to 50 atmospheres with carbon monoxide. Agitation is commenced and the autoclave and contents are heated to 50°C and kept at this temperature for ca. 8 hours. The autoclave is then cooled and vented and the contents are discharged. Gas-liquid chromatography of the product shows over 90% conversion of the nitro compound to aniline.

In the absence of the rhodium carbonyl catalyst only a trace amount of aniline is formed.

EXAMPLE 21

In place of rhodium carbonyl of Example 20, there is used triruthenium dodecacarbonyl as catalyst. The yield of aniline obtained is ca. 7–9%.

EXAMPLE 22

In place of rhodium carbonyl of Example 20, there is used a catalyst based on a mixture of oxides of silver and manganese and prepared after Dodman et al. (U.S. Pat. No. 3,637,820, Example 11). The yield of aniline is ca. 4–5%.

TABLE III

| Run No. | Catalyst | Nitrogen Containing Compound | Temp. °C | CO atm. | Time (hours) | Conversion % | Aniline Yield % |
| --- | --- | --- | --- | --- | --- | --- | --- |
| 1 | $[Rh(CO)_2Cl]_2$ | Pyridine | 150 | 120 | 3 | 100 | >90 |
| 2 | $Rh_6(CO)_{16}$ | N-methylpyrrolidine | 150 | 120 | 3 | 100 | >90 |
| 3 | $Rh_2O_3$ | Pyridine | 150 | 120 | 3 | 100 | >90 |
| 4 | $Rh_6(CO)_{16}$ | N-methylpyrrolidine | 160 | 80 | ½ | 100 | >90 |
| 5 | " | " | 50–60 | 50 | 12 | ~95 | ~90 |

TABLE III-continued

| Run No. | Catalyst | Nitrogen Containing Compound | Temp. °C | CO atm. | Time (hours) | Conversion % | Aniline Yield % |
|---|---|---|---|---|---|---|---|
| 6 | " | Pyridine | 60 | 50 | 12 | ~ 5 | > 5 |
| 7(b) | " | N-methylpyrrolidine | 60 | 50 | 12 | 8 | ~ 4 |

(b)absence of water

While the invention has been described with reference to particular embodiments thereof, it will be appreciated that modification and variations are possible without departing from the invention.

What is claimed:

1. In a process for the preparation of aromatic primary amine which comprises reducing an aromatic nitro compound with carbon monoxide and water under reaction conditions, the improvement which comprises conducting the reaction in the presence of a basic nitrogen containing compound selected from the group consisting of a tertiary amine and an amide and a rhodium catalyst selected from the group consisting of rhodium oxide, rhodium hydroxide, a rhodium carbonyl compound and a rhodium salt which forms a rhodium carbonyl compound under reduction conditions.

2. The process of claim 1 wherein the reaction is carried out at a temperature in the range of from about 50° to about 150°C.

3. The process of claim 1 wherein the reduction is carried out at a carbon monoxide pressure of in the range of from about 50 to about 120 atmospheres.

4. The process of claim 1 wherein the nitrogen compound is employed in the proportion of at least 6 moles per mole of the said nitro compound.

5. The process of claim 1 wherein the nitrogen compound is a tertiary amine.

6. The process of claim 5 wherein the tertiary amine has a dissociation constant in aqueous solution of at least pKa = 10.

7. The process of claim 5 wherein the tertiary amine is N-methylpyrrolidine.

8. The process of claim 5 wherein the tertiary amine is pyridine.

9. The process of claim 1 wherein the catalyst is a rhodium carbonyl compound.

10. The process of claim 1 wherein the catalyst is rhodium oxide and the reduction is carried out at a temperature above about 150°C and at a carbon monoxide pressure of above 100 atmospheres.

11. In a process for preparing an aromatic primary amine by catalytic reduction of an aromatic nitro compound having a nitro group available for reduction to an amino group, using a metal carbonyl catalyst of Group VIII metal and carbon monoxide, the improvement which comprises heating said nitro compound in homogeneous liquid phase in the presence of a rhodium carbonyl compound as a catalyst, water as a hydrogen source and a basic tertiary amine or amide as a solvent.

12. A process of claim 11 wherein said rhodium carbonyl compound is formed it situ from rhodium oxide, rhodium hydroxide, or a rhodium salt capable of forming said rhodium carbonyl compound in the reaction.

* * * * *